United States Patent [19]

Watkins et al.

[11] Patent Number: 4,604,612
[45] Date of Patent: Aug. 5, 1986

[54] ICE DETECTOR

[75] Inventors: Roger D. Watkins, Wantage; Arthur B. Gillespie, Abingdon; Michael O. Deighton, Reading; Roger B. Pike, Newbury; Colin B. Scott-Kestin, Reading, all of England

[73] Assignee: United Kingdom Atomic Energy Authority, London, England

[21] Appl. No.: 516,262

[22] Filed: Jul. 22, 1983

[30] Foreign Application Priority Data

Aug. 3, 1982 [GB] United Kingdom ............... 8222419
Dec. 16, 1982 [GB] United Kingdom ............... 8235668

[51] Int. Cl.$^4$ .............. G08B 19/02; G01H 3/12; H04R 15/00; H04R 17/00
[52] U.S. Cl. .................. 340/582; 73/599; 367/157; 367/168; 367/908
[58] Field of Search ............ 340/582, 962, 580, 581, 340/583; 73/599; 367/908, 157, 168

[56] References Cited

U.S. PATENT DOCUMENTS

| 2,956,184 | 10/1960 | Pollack | 367/157 X |
| 3,240,054 | 3/1966 | Roth | 340/582 X |
| 3,409,869 | 11/1968 | McCool et al. | 367/157 X |
| 3,512,400 | 5/1970 | Lynnworth | 73/599 X |
| 3,612,924 | 10/1971 | Semmelink | 367/168 X |
| 3,706,981 | 12/1972 | Hart | 340/582 |
| 3,781,566 | 12/1973 | Meuller | 340/582 X |
| 3,854,060 | 12/1974 | Cook | 367/157 X |
| 4,054,255 | 10/1977 | Magenheim | 340/580 X |
| 4,253,337 | 3/1981 | Vasile | 73/599 |
| 4,376,302 | 3/1983 | Miller | 367/157 |
| 4,404,852 | 9/1983 | Goto | 340/582 X |
| 4,461,178 | 7/1984 | Chamuel | 340/582 X |

FOREIGN PATENT DOCUMENTS

| 0018280 | 10/1980 | European Pat. Off. . |
| 564513 | 10/1944 | United Kingdom . |
| 1117664 | 6/1968 | United Kingdom . |
| 2060883 | 5/1981 | United Kingdom . |
| 2070772 | 9/1981 | United Kingdom . |

OTHER PUBLICATIONS

Kasahara et al., "Frost Sensor", Japanese *National Technical Report*, vol. 24, No. 3, pp. 512-518, Jun. 1978.

Primary Examiner—James L. Rowland
Assistant Examiner—Thomas J. Mullen, Jr.
Attorney, Agent, or Firm—William R. Hinds

[57] ABSTRACT

An ice detector to detect a lyaer of ice on a thin solid sheet 14, such as the skin of an aircraft wing, even in the presence of water, comprises two ultrasonic transducers attached to the sheet. The first transducer 10 is adapted to cause propagation of ultrasonic waves through the sheet 14 having their predominant component parallel to the surface of the sheet 14. Such waves will dissipate energy into an ice layer adhering to the surface, but not into air or a liquid layer. The second transducer 30 is adapted to detect the waves propagating in the sheet and to give a signal representative of their amplitude. A discriminator 34 responsive to the signal detects the presence of an ice layer on the surface.

14 Claims, 3 Drawing Figures

ICE DETECTOR

This invention relates to instruments for detecting the presence of ice on a surface, in particular on a wing of an aircraft.

In winter conditions an aircraft may be subjected to rain and snow, and a layer of ice may form on the aircraft's wings. Such an ice layer can be hazardous to safe operation of the aircraft, causing the aircraft to crash on take-off for example.

According to the invention there is provided a method for detecting ice on a surface of a thin solid sheet comprising, energising a transducer to cause propagation through a portion of the sheet of ultrasonic waves having their predominant component parallel to the surface of the sheet, detecting the waves by means of a second transducer, measuring the amplitude of the waves received by the second transducer, and detecting by means of the amplitude of the waves received by the second transducer the presence of a layer of ice on the surface of the portion of the sheet.

If a layer of ice forms on the surface, the amplitude and intensity of the waves detected by the second transducer will decrease, as waves having their predominant component parallel to the surface will dissipate energy into the ice layer but will not dissipate energy into air or a liquid layer.

According to the invention there is also provided an ice detector to detect ice on a surface of a thin solid sheet, comprising an ultrasonic transducer adapted to cause propagation through a portion of the sheet of ultrasonic waves having their predominant component parallel to the surface of the sheet, an ultrasonic transducer adapted to receive the waves and create a signal representative of the amplitude thereof, and means responsive to the signal to detect the presence of an ice layer on the surface of the portion of the sheet.

The waves may be horizontally polarized guided shear waves; or the waves may be a mode of Lamb wave whose predominant component is horizontal. In this context the term horizontal means parallel to the surface, while vertical means normal to the surface.

The transducers may be attached to the opposite surface of the portion of the sheet to that on which an ice layer may develop, and may be generated and received by piezoelectric or electromagnetic means.

An ice detector embodying the invention will now be described by way of example only and with reference to the accompanying drawings in which.

Figure 1:
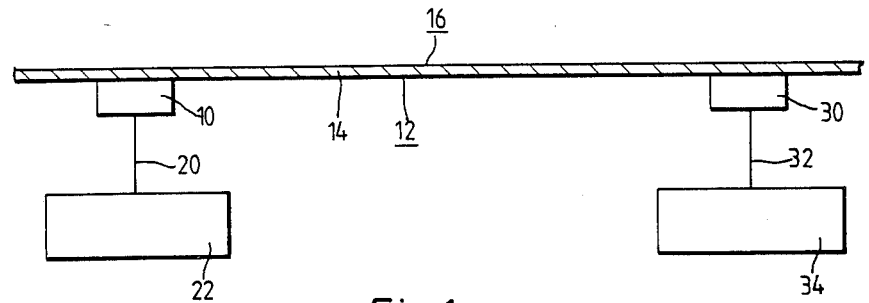
FIG. 1 is a diagrammatic view of an ice detector attached to a metal sheet.

As shown in FIG. 1, an ice detector comprises a first transducer 10 attached to one surface 12 of a metal sheet 14, opposite the surface 16 on which icing is expected to occur. The transducer 10 is connected by a coaxial cable 20 to a signal generator 22, which when energised causes the transducer 10 to oscillate at a frequency such as to cause pulses of horizontally polarized shear waves to propagate through the sheet 14 with a wavelength comparable with the thickness of the sheet 14, so that the shear waves are guided by the surfaces 12 and 16. A second transducer 30 identical to the first transducer 10 is attached to the surface 12 of the sheet 14 at a distance from the transducer 10. The second transducer 30 is connected by a coaxial cable 32 to a signal receiver and discriminator 34 for determining whether or not an ice layer exists on the surface 16 from a measurement of the amplitude of the signals from the second transducer 30.

Figure 2:
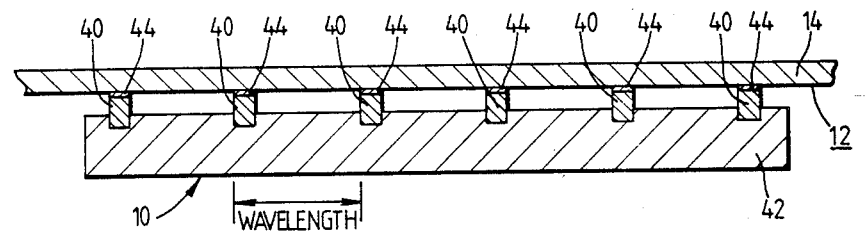
FIG. 2 is a sectional view, parallel to the plane of FIG. 1, of one of the transducers of the ice detector.

As shown in FIG. 2 the transducer 10 comprises six transducer strips 40 parallel to each other extending perpendicular to the plane of the Figure and spaced apart at a distance equal to the wavelength of the ultrasonic shear waves in the sheet 14, held in a solid matrix 42. Each strip 40 is of length 30 mm and is bonded to the surface 12 by an electrically conducting layer 44. Each strip 40 is made of a piezo electric material and has contacts on opposing top and bottom surfaces (not shown) by means of which it can be excited into vibrations parallel to its length. These vibrations are in phase with the other strips 40, and cause horizontally polarised shear waves to propagate in the sheet 14.

The transducer 30 is of identical construction to the transducer 10. A shear wave propagating in the sheet 14 drives each of the strips 40 of the transducer 30 into vibrations parallel to its length, thereby inducing a voltage between the contacts on the top and bottom surfaces of the strips 40 of the transducer 30.

In operation of the ice detector the signal generator 22 is energised to produce a chopped continuous wave, the number of cycles in each burst being approximately equal to the number of transducer strips 40 in each of the transducers 10 and 30, so that the first transducer 10 causes pulses of horizontally polarised ultrasonic shear waves to propagate through the sheet 14. The pulses are received by the second transducer 30 which sends a signal, representative of the amplitude of the pulses, to the signal receiver and discriminator 34. To ensure that the signal receiver and discriminator 34 responds only to a signal corresponding to a pulse which has travelled directly from the first transducer 10 to the second transducer 30, the signal receiver and discriminator 34 is gated to operate within a time interval about 5% on either side of the expected time of arrival of the pulse. If the surface 16 is dry, or covered in water (in which horizontally polarised shear waves cannot propagate) the pulses will have a larger amplitude than if the surface 16 is covered by a layer of ice, in which shear waves can propagate. This is because some of the energy of the shear wave pulse in the sheet 14 will be dissipated in causing waves to propagate through the ice. Thus the ice detector can detect ice adhering to the surface 16 but is insensitive to the presence of water.

The frequency of the continuous wave produced by the signal generator 22 depends on the mode of wave which it is desired to propagate through the sheet 14. For example, for a zero-order symmetrical horizontally polarised shear wave a frequency in the range 250 kHz to 1 MHz may be used. The pulse repetition frequency is limited by reverberation of the pulses, but may conveniently be 50 Hz. The distance between the first transducer 10 and the second transducer 30 along the sheet 14 might be as large as 5 or 10 meters, although this depends on the material of which the sheet 14 is made, and on the sensitivity of the signal receiver and discriminator 34.

The sensitivity of the ice detector to different thicknesses of ice depends upon the frequency (and hence the wavelength) of the ultrasonic waves. It has been found that an ice detector generating zero-order symmetrical horizontally polarised shear waves and operating at 1 MHz is sensitive to an ice layer about half as thick as that to which a similar ice detector operating at 500 kHz is sensitive. The frequency of operation of the ice detector can therefore be chosen to provide a required sensitivity.

Figure 3:
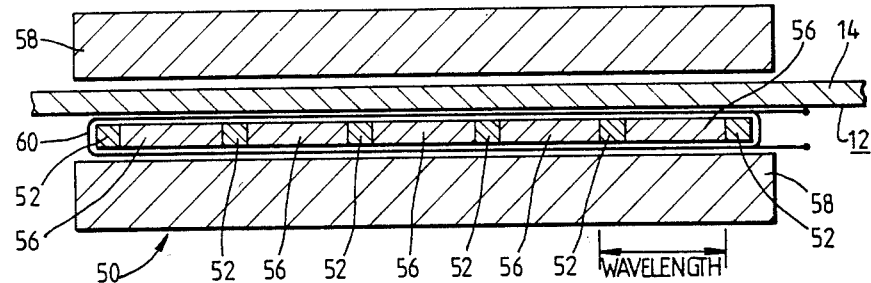
FIG. 3 is a sectional view of an alternative transducer to that of FIG. 2.

It will be understood that alternative types of transducer may be used to generate the horizontally polarised shear waves and in FIG. 3, to which reference is now made, is shown an electromagnetic transducer 50 which may be used in place of the transducers 10 and 30 on a metal sheet 14. The electromagnetic transducer 50 comprises six strips 52 of soft ferromagnetic material extending parallel to each other and perpendicular to the plane of the Figure, of length 30 mm, and spaced apart at a distance equal to the wavelength of the ultrasonic shear waves in the sheet 14 by spacers 56 of non-ferromagnetic material. Two ceramic magnets 58, one on each side of the sheet 14, produce a magnetic field perpendicular to the surface of the sheet 14 which is strongest adjacent to the ferromagnetic strips 52. A coil 60 of ten turns of wire is wound around the ferromagnetic strips 52 and the spacers 56, a part of each turn lying adjacent to one surface 12 of the sheet 14 and parallel to the plane of the Figure. The ferromagnetic strips 52 and the coil 60 are located adjacent to the surface 12 of the sheet 14 but are not bonded to it.

An alternating current (from a source which is not shown in the Figure) flowing in the coil 60 induces eddy currents in the surface 12 of the sheet 14 parallel to the plane of the Figure, so that the portions of the surface 12 adjacent to the ferromagnetic strips 52 experience forces perpendicular to the plane of the Figure, and so shear waves are caused to propagate in the sheet 14. Similarly, a shear wave propagating in the sheet 14 adjacent to the ferromagnetic strips 52 will induce an alternating electromotive force in the coil 60.

An ice detector utilizing two transducers 50 in place of the transducers 10 and 30 operates in the same manner as that described above in relation to the ice detector of FIGS. 1 and 2.

It will be appreciated that although the transducers 10, 30 and 50 have been described as comprising six strips 40 or 52, a different number of strips may be found more convenient. Each transducer may have as few as one strip, but for adequate selectivity of ultrasonic wave mode a number greater than five is preferable.

It will be appreciated also that the length of each strip 40 or 52 determines the directivity of the transducer 10, 30 or 50, but that the length may also be dictated by installation constraints. In the transducers 10, 30, and 50 the strips are of length thirty millimeters, but, for example, strips of length between 10 mm and 50 mm may be convenient. The width of the strips is preferably equal to about a fifth of the wavelength of the ultrasonic waves generated, but the strips may be of any convenient width less than about half the wavelength.

It will be understood that other modes of wave may be caused to propagate in the sheet 14. For example a mode of Lamb wave having its predominant component parallel to the surface may be used.

It will also be understood that as long as the wavelength of the ultrasonic waves is comparable to the thickness of the sheet then the ultrasonic waves will be guided by the surfaces of the sheet, and the transducers 10, 30 or 50 may be situated on either side of the sheet.

It will also be appreciated that once a layer of ice is detected on the surface 16 of the sheet 14 by the ice detector, then the thickness of the ice layer may if desired be measured by a conventional thickness gauge monitor (not shown) attached to the sheet 14 at a position between the first and the second transducers of the ice detector.

We claim:

1. A method for detecting ice on a surface of a thin solid sheet comprising, energising a transducer to cause propagation through a portion of the sheet of ultrasonic waves having their predominant component parallel to the surface of the sheet, detecting the waves by means of a second transducer, measuring the amplitude of the waves received by the second transducer, and detecting by means of the amplitude of the waves received by the second transducer the presence of a layer of ice on the surface of the portion of the sheet.

2. A method as claimed in claim 1 wherein the waves are horizontally polarized guided shear waves.

3. A method as claimed in claim 1 wherein the waves are a mode of Lamb wave whose predominant component is horizontal.

4. A method as claimed in claim 1 wherein the frequency of the waves is chosen to provide a desired sensitivity to thickness of the ice layer.

5. An ice detector to detect ice on a surface of a thin solid sheet, comprising an ultrasonic transducer adapted to cause propagation through a portion of the sheet of ultrasonic waves having their predominant component parallel to the surface of the sheet, an ultrasonic transducer adapted to receive the waves and create a signal representative of the amplitude thereof, and means responsive to the signal to detect the presence of an ice layer on the surface of the portion of the sheet.

6. An ice detector as claimed in claim 5 wherein the waves are horizontally polarized guided shear waves.

7. An ice detector as claimed in claim 5 wherein the waves are a mode of Lamb wave whose predominant component is horizontal.

8. An ice detector as claimed in claim 5 wherein the frequency of the waves is chosen to provide a desired sensitivity to thickness of the ice layer.

9. An ice detector as claimed in claim 5 wherein the ultrasonic transducers are acoustically coupled to the opposite surface of the portion of the sheet to that on which an ice layer may form.

10. An ice detector as claimed in claim 5 wherein the ultrasonic transducers are piezoelectric transducers.

11. An ice detector as claimed in claim 10 wherein each transducer includes at least six piezoelectric strips parallel to one another and parallel and adjacent to the surface of the sheet.

12. An ice detector as claimed in claim 5 wherein the ultrasonic transducers are electromagnetic transducers.

13. An ice detector as claimed in claim 12 wherein each transducer comprises at least six ferromagnetic strips parallel to one another and parallel and adjacent to the surface of the sheet, and an exciting coil.

14. An ice detector to detect ice on a surface of a thin solid sheet comprising:
 (a) a first ultrasonic transducer acoustically coupled to the surface of the sheet opposite to the surface on which an ice layer may form, and adapted when energised to cause propagation through a portion of the sheet of horizontally polarized guided ultrasonic shear waves of a frequency between 250 kHz and 1 MHz;
 (b) a second ultrasonic transducer acoustically coupled to the said opposite surface of the sheet, and adapted to receive the ultrasonic waves propagating through the portion of the sheet and to create a signal representative of the amplitude of said ultrasonic waves; and (c) means responsive to the signal to detect the presence of an ice layer on the surface of the portion of the sheet;

wherein the frequency is chosen to provide a desired sensitivity to thickness of the ice layer, and each transducer comprises a plurality of linear transducer elements arranged adjacent to the said opposite surface, aligned parallel to each other at a spacing about equal to the wavelength of the ultrasonic waves of the chosen frequency propagating in the sheet.

* * * * *